(12) United States Patent
Chapman

(10) Patent No.: US 7,500,646 B2
(45) Date of Patent: Mar. 10, 2009

(54) LIGHT TOOL MOUNT ASSEMBLY

(75) Inventor: Lawrence J. Chapman, Earlville, IA (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 11/689,061

(22) Filed: Mar. 21, 2007

(65) Prior Publication Data

US 2008/0230667 A1    Sep. 25, 2008

(51) Int. Cl.
*E04G 3/00* (2006.01)

(52) U.S. Cl. .................... 248/279.1; 248/481

(58) Field of Classification Search .............. 248/279.1, 248/278.1, 288.31, 288.51, 481, 482, 181.1, 248/181.2; 403/374.3, 74.4
See application file for complete search history.

(56) References Cited

U.S. PATENT DOCUMENTS

| | | | | |
|---|---|---|---|---|
| 3,622,112 A | * | 11/1971 | Stroh | 248/181.1 |
| 3,633,949 A | * | 1/1972 | Pfluger | 403/343 |
| 4,669,911 A | * | 6/1987 | Lundgren et al. | 403/344 |
| 5,118,058 A | * | 6/1992 | Richter | 248/183.2 |
| 5,419,522 A | * | 5/1995 | Luecke et al. | 248/288.51 |
| 5,560,577 A | * | 10/1996 | Keselman | 248/279.1 |
| 6,921,226 B2 | * | 7/2005 | Rundle et al. | 403/77 |
| 2002/0175256 A1 | * | 11/2002 | Louh | 248/309.1 |
| 2006/0198040 A1 | * | 9/2006 | Branham et al. | 359/881 |

* cited by examiner

*Primary Examiner*—Ramon O Ramirez
(74) *Attorney, Agent, or Firm*—Mark W. Croll; Donald J. Breh; Levenfeld Pearlstein, LLC

(57) ABSTRACT

A mount for a light tool having a bore is for use at an associated tool station. The ball joint has a ball for engaging a socket joint. The ball joint has a stub extending therefrom and a wedge-lock element having a collar for engaging the stub. A carriage is mounted to the collar. A pair of finger elements are mounted to the carriage for pivotal movement relative to the carriage, toward and away from each other. The wedge lock element includes a wedge movable along the axis between the fingers to urge the fingers outward as the wedge moves toward the carriage. The wedge lock element is positioned with at least a portion of the carriage and the fingers in the tool bore and the wedge is drawn in to secure the ball joint portion in the tool bore. A clamp element is operably connected to the ball joint portion to indirectly secure the ball joint to a fixture. The clamp element includes a front plate, a bracket and a brake element disposed and movable between the front plate and the brake element. The brake is movable toward a front wall of the fixture to secure the clamp to the fixture.

11 Claims, 2 Drawing Sheets

LIGHT TOOL MOUNT ASSEMBLY

BACKGROUND OF THE INVENTION

The present invention relates to a tool mount assembly. More particularly, the present invention relates to a mount assembly for use with a light tool.

Systems are known to provide mounting capabilities for a wide variety of items. For example, systems are available to mount a computer, personal digital assistant (PDA), global positioning system (GPS) device or the like to a vehicle dashboard or windshield. One family of mounts is currently available from Ram Mounting Systems of Seattle, Wash. These mounts or mounting systems permit mounting a device, permanently or temporarily to many different surfaces.

Typically, a mount includes various joints, such as ball and socket joints, hinges and the like to permit articulating elements relative to one another. For example, one such mount includes a base that is attached to a surface and an arm hingedly mounted to the base. A socket joint is mounted to the arm. A ball mounts to the device (by, for example, a carrier or threaded element engaging the device) that inserts into the socket. The device can thus be manipulated relative to the surface on which it is mounted.

In the testing industry, blacklights or ultraviolet (UV) lights are used to identify imperfections in machined parts. For example, in magnetic particle inspection, a solution is applied to a part that is subject to UV light. Imperfections such as cracks, fissures and the like are then visible under this light.

Most lights are hand-held, and thus a part is not easily manipulated (turned, rotated or the like) to permit inspection. One known mounting system includes a post with a stalk onto which the light is mounted. However, such systems do not afford great flexibility for lighting desired areas. It is often desired to mount the light at an inspection station, and to be able to move the light, so that it can be directed at the part.

Accordingly, there is a need for a light mount assembly that provides a high amount of flexibility and maneuverability. Desirably, such a mount assembly is used with standard, known mounting system components. More desirably, such a mount assembly permits locating the light at a specific, desired location and securely clamping the light at that location.

BRIEF SUMMARY OF THE INVENTION

A mount for a light tool is for use at an associated tool station. The light tool has a bore therein, preferably in the tool handle. The mount includes a ball joint portion having a ball for engagement with an associated socket joint. The ball joint portion has a stub extending therefrom. Preferably the stub is threaded.

A wedge-lock element has a collar for engaging the stub. A preferred collar has a mating thread. A carriage is mounted to the collar to define a longitudinal axis. A pair of finger elements are mounted to the carriage for pivotal movement relative to the carriage. The fingers move toward and away from the axis and thus each other.

The wedge lock element includes a wedge movable along the axis between the fingers to urge the fingers outward as the wedge moves inward toward the carriage. In a present mount, the fingers include locking tabs extending outwardly from free ends of the fingers.

The wedge lock element is positioned with at least a portion of the carriage and the fingers in the tool bore and the wedge is drawn in, between the fingers, urging the fingers outwardly to secure the wedge-lock element in the tool bore. The ball portion is threaded into the collar to mount the ball portion to the tool handle.

The mount can include a threaded element mounted for rotation in the carriage that threadedly engages the wedge, such that rotation of the rod moves the wedge longitudinally toward and away from the carriage. Access to rotate the rod is through the collar.

A biasing element biases the fingers toward one another. The biasing element can be a band encircling the fingers, such as a resilient band. The fingers are pivotally mounted to the carriage.

The mount can include a clamp element operably connected to the ball joint portion by, for example, an articulating arm having a socket joint thereon. The clamp element can be adapted to indirectly secure the ball joint portion to a fixture. The clamp includes a front plate, a bracket parallel to and spaced from the front plate (on which the arm is mounted), and a brake element disposed and movable between the front plate and the brake element. The brake element is movable toward a front wall of the fixture to secure the clamp element to the fixture.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

While the present invention is susceptible of embodiment in various forms, there is shown in the figures and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 1:
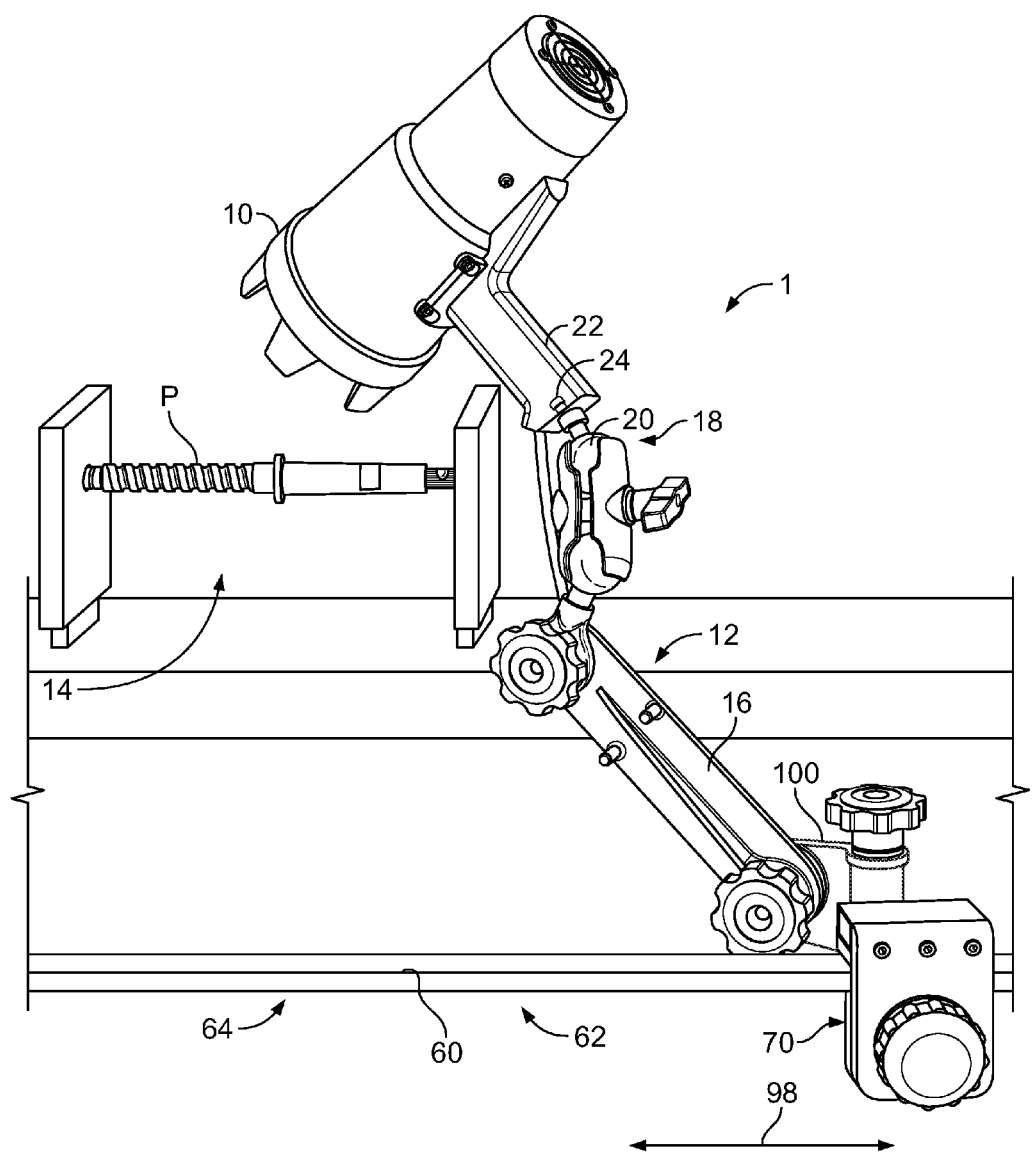
FIG. 1 is an illustration of the light tool mount assembly embodying the principles of the present invention, the mount being shown mounted to an inspection station.
Figure 2:
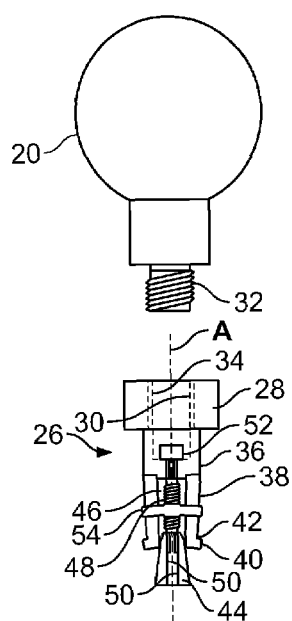
FIG. 2 is a front view, in partial cross-section, of the ball and wedge-lock element of the mount.
Figure 3A:
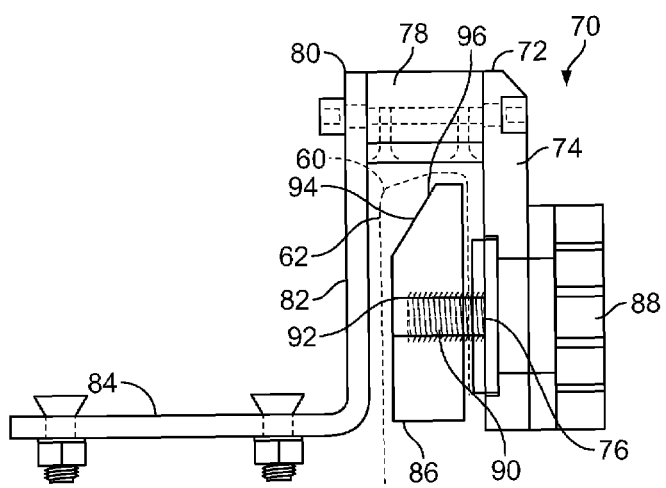
FIGS. 3A and 3B are side and front views, respectively, of the clamp assembly of the present invention.
Figure 3B:
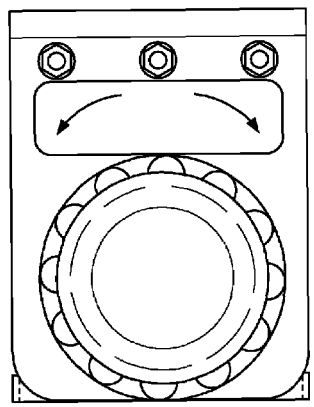

Referring now to the figures and in particular to FIG. 1 there is shown an exemplary blacklight or ultraviolet (UV) light 10 in a mount 12, for use in an inspection station 14. The light 10 can be a commercially available model, such as a ZB-100F commercially available from Magnaflux, an ITW Company, of Glenview, Ill.

In that the light 10 is used to detect imperfections and the like in a machined part P, it is desirable to be able to direct the light 10 at specific areas of the part P. The present mount 12 uses parts of known mount systems, that is, articulating arms 16 and, for example, socket joints 18 in conjunction with novel tool mounts and arm mounts and clamps to provide a flexible and easily manipulated tool mount system 1.

A ball 20 for engagement with the mount socket 18 is mounted to the tool (light) 10, likely at the tool handle 22. The ball 20 is mounted to the tool handle 22 at a hole or opening 24 using a wedge-lock element 26. The wedge-lock element 26 includes a base collar 28 having an opening 30 to which the ball 20 is mounted. The ball 20 includes a stub, such as the a threaded stub 32 extending therefrom for threadedly engaging the mating thread 34 in the collar opening 30. It will be appreciated that other mounting configurations, such as bayonet mounts and the like, can also be used. A carriage 36 is mounted to the collar 28. The collar 28 and carriage 36 are collinear as indicated by the axis A.

The element 26 includes a pair of finger elements 38 mounted to the carriage 36 for pivoting movement relative to the collar 28. The fingers 38 include locking tabs 40 at free ends 42 of the fingers 38 that project outwardly from the fingers 38.

A wedge element 44 is disposed for movement between the fingers 38 to move or urge the fingers 38 outwardly. The wedge 44 is moved up into the space 46 between the fingers 38 by a threaded rod 48 (such as a bolt or the like), that is longitudinally stationary in the carriage 36, but moves the wedge 44 toward and away from the carriage 36. To effect this movement, the wedge 44 has an internal thread 50 that is engaged by the rod 48. As the wedge 44 moves toward the carriage 36, between the fingers 38, the fingers 38 are urged outward. As the wedge 44 is moved away from the carriage 36, the fingers 38 are permitted to "close" or move toward one another. In this manner, the wedge 44 moves (linearly) longitudinally between the fingers 38 with the rotational movement of the rod 48. A head or engaging portion 52 of the rod 48 is mounted in the carriage 36, between the fingers 38, and is accessed through the opening 30 in the collar 28.

The fingers 38 are maintained biased toward one another. As such, as the rod 48 is rotated to move the wedge 44 deeper between the fingers 38, the wedge 44 works against the bias. However, the bias also tends to draw the fingers 38 together, to prevent the wedge-lock 26 from binding in the tool handle bore 24. The bias can be provided by a resilient element (such as an elastic member 54) positioned around the fingers 38.

In using the present mount 12, the wedge-lock portion 26 (with the ball 20 removed) is positioned in the handle opening 24. The wedge-lock 26 must be in the retracted state (that is with the wedge 44 withdrawn from between the fingers 38) to insert the wedge-lock 26 into the opening 24. When the wedge-lock 26 is positioned in the handle 22, the rod 48 is rotated (as by rotating the head 52). In a likely arrangement, the rod 48 is rotated clockwise to draw the wedge 44 upwardly, between the fingers 38. The wedge 44 is drawn up tight into the fingers 38 to secure the wedge-lock 26 in the handle 22. The locking tabs 40 engage the inside surface of the handle opening 24 and secure (or lock) the wedge-lock 26 to the handle 22. The ball stub 32 can then be threaded into the collar opening 30 to secure the ball 20 to the tool 10. Because the ball stub 32 to collar 28 joint is a metal to metal connection, there is much less opportunity for wear and stripped threads than, for example, a threaded connection in a plastic light tool handle.

The ball 20 is mounted in a known socket 18, which in turn is mounted to an arm 16. In order to be most effective and to provide the greatest flexibility in directing light from the light 10, the arm 16 is mounted for movement along an upper edge or lip 60 of the front surface 62 of a fixture 64, such as an inspection table.

The mount 12 includes a clamp 70 having a body 72 that includes a front plate 74 having an opening 76. An upper base 78 is mounted to the top of the plate 74 and a bracket 80 is mounted to a side of the base 78 opposite the front plate 74. The bracket 80 includes a downwardly extending plate 82 (parallel to and spaced from the front plate 74) and a lower, rearwardly extending leg 84. The arm 16 is mounted to the plate leg 84.

A brake 86 is mounted between the front plate 74 and bracket 80. A rotatable knob 88 is mounted to the brake 86 to permit the brake 86 to be moved laterally, between the front plate 74 and bracket 80. A threaded shaft 90 is mounted to the knob 88 that threads into an opening 92 in the brake 86. The brake 86 has a cut-out section 94 at an upper corner to accommodate mounting the clamp 70 to the fixture 64.

In use, the clamp 70 is attached to the fixture front wall 62, over the outwardly rolled lip 60. The clamp 70 is positioned with the clamp body 72 over the lip 60 with the fixture front wall 62 between the clamp front plate 74 and the bracket 80. The brake 86 is positioned between the fixture front wall 62 and the clamp front plate 74. The knob shaft 90 is inserted through the front plate opening 76 and is threadedly engaged with the brake 86. As the knob 88 is rotated, the brake engages the fixture front wall 62 to secure the mount 12 to the fixture 62.

The mount 12 can be positioned along the front wall 62 (moving laterally along the front wall as indicated by the arrow at 98, and locked thereto by the clamp 70). Various adjustments can be made to the arm 16, for example at the ball and socket joints 18 or at the other pivoting or hinged joints 100, to position the light 10 in a desired location and orientation.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the claims.

What is claimed is:

1. A mount for a light tool for use at an associated tool station, the light tool having a bore therein, the mount comprising:

a ball joint portion having a ball for engagement with an associated socket joint, the ball joint portion having a stub extending therefrom; and a wedge-lock element, the wedge-lock element having a collar for engaging the stub, a carriage mounted to the collar to define a longitudinal axis and a pair of finger elements mounted to the carriage for pivotal movement relative to the carriage, toward and away from the axis and each other, the wedge lock element including a wedge movable along the axis between the fingers to urge the fingers outward as the wedge moves toward the carriage, wherein the wedge lock element is positioned with at least a portion of the carriage and the fingers in the tool bore and the wedge is drawn in, between the fingers, urging the fingers outwardly to secure the wedge-lock element in the tool bore to secure the ball joint portion in the tool bore.

2. The mount in accordance with claim 1 wherein the stub is threaded and the collar has a mating thread for threaded engagement of the stub and collar.

3. The mount in accordance with claim 1 wherein the fingers include locking tabs extending outwardly from free ends of the fingers.

4. The mount in accordance with claim 1 including a threaded element mounted for rotation in the carriage and threadedly engaging the wedge, wherein rotation of the rod moves the wedge longitudinally toward and away from the carriage.

5. The mount in accordance with claim 4 wherein access to rotate the rod is through the collar.

6. The mount in accordance with claim 1 including a biasing element for biasing the fingers toward one another.

7. The mount in accordance with claim 6 wherein the biasing element is a band encircling the fingers.

8. The mount in accordance with claim 7 wherein the band is resilient.

9. The mount in accordance with claim 1 wherein the fingers are pivotally mounted to the carriage.

10. The mount in accordance with claim 1 including a clamp element operably connected to the ball joint portion, the clamp element adapted to indirectly secure the ball joint portion to a fixture, the clamp element including a front plate, a bracket parallel to and spaced from the front plate, and a brake element disposed and movable between the front plate and the brake element, the brake element movable toward a front wall of the fixture to secure the clamp element to the fixture.

11. The mount in accordance with claim 10 wherein the clamp element includes a knob operably connected to the brake element to move the brake element into and out of engagement with the fixture front wall.

\* \* \* \* \*